(12) United States Patent
O'Sullivan et al.

(10) Patent No.: US 9,320,502 B2
(45) Date of Patent: Apr. 26, 2016

(54) CYTOLOGY BALLOON

(71) Applicant: Cook Medical Technologies, LLC, Bloomington, IN (US)

(72) Inventors: Donagh O'Sullivan, Co. Tipperary (IE); Alison Liddy, Galway (IE)

(73) Assignee: Cook Medical Technologies LLC, Bloomington, IN (US)

( * ) Notice: Subject to any disclaimer, the term of this patent is extended or adjusted under 35 U.S.C. 154(b) by 222 days.

(21) Appl. No.: 13/796,905

(22) Filed: Mar. 12, 2013

(65) Prior Publication Data

US 2014/0276199 A1 Sep. 18, 2014

(51) Int. Cl.
*A61B 10/02* (2006.01)
*A61B 17/3207* (2006.01)
*A61M 25/10* (2013.01)
*A61B 10/04* (2006.01)

(52) U.S. Cl.
CPC .......... *A61B 10/02* (2013.01); *A61B 17/320725* (2013.01); *A61M 25/10* (2013.01); *A61B 10/04* (2013.01); *A61M 2025/1075* (2013.01); *A61M 2025/1086* (2013.01)

(58) Field of Classification Search
CPC . A61B 10/04; A61B 10/0045; A61B 10/0096
USPC ......................................................... 500/562
See application file for complete search history.

(56) References Cited

U.S. PATENT DOCUMENTS

| | | | |
|---|---|---|---|
| 3,996,938 A | 12/1976 | Clark, III | |
| 4,465,072 A | 8/1984 | Taheri | |
| 4,771,776 A * | 9/1988 | Powell et al. | 606/194 |
| D300,060 S | 2/1989 | Molgaard-Nielsen | |
| 4,927,412 A | 5/1990 | Menasche | |
| 4,958,621 A | 9/1990 | Topel et al. | |
| 4,989,614 A | 2/1991 | Dejter, Jr. et al. | |
| 5,037,379 A | 8/1991 | Clayman et al. | |
| 5,048,538 A | 9/1991 | Terwilliger et al. | |
| 5,060,658 A | 10/1991 | Dejter, Jr. et al. | |
| 5,083,572 A | 1/1992 | Pokorny | |
| 5,146,921 A | 9/1992 | Terwilliger et al. | |
| 5,249,583 A | 10/1993 | Mallaby | |
| 5,253,652 A | 10/1993 | Fast | |
| 5,287,587 A | 2/1994 | Mann | |
| 5,409,012 A * | 4/1995 | Sahatjian | 600/562 |
| 5,423,745 A | 6/1995 | Todd et al. | |
| D360,260 S | 7/1995 | Brandt | |
| 5,488,958 A | 2/1996 | Topel et al. | |
| D369,857 S | 5/1996 | Booth et al. | |
| 5,535,756 A | 7/1996 | Parasher | |
| 5,702,413 A | 12/1997 | Lafontaine | |
| 5,713,369 A | 2/1998 | Tao et al. | |

(Continued)

*Primary Examiner* — Adam J Eiseman
*Assistant Examiner* — Patrick Fernandes
(74) *Attorney, Agent, or Firm* — Brinks Gilson & Lione

(57) ABSTRACT

A medical device for collecting cells includes an inflatable balloon and a perforated sleeve surrounding the balloon. The sleeve includes a plurality of openings therein for collecting cells when inserted into a body cavity. The balloon and sleeve can be housed in a sheath in a compressed delivery condition for being delivered to a target site for cell collection. The balloon and sleeve can then be inflated to expand into contact with the target site. The openings in the sleeve create a mildly abrasive surface for enhancing cell collection while limiting patient trauma. The balloon and sleeve can be reciprocated back and forth to collect cells from the surface of the body cavity. The balloon and sleeve having the collected cells can then be deflated and retracted from the body cavity.

27 Claims, 3 Drawing Sheets

(56) References Cited

U.S. PATENT DOCUMENTS

| | | |
|---|---|---|
| 5,749,883 A | 5/1998 | Halpern |
| 5,797,953 A | 8/1998 | Tekulve |
| 5,843,027 A * | 12/1998 | Stone et al. .................. 604/509 |
| 6,346,086 B1 | 2/2002 | Maksem et al. |
| 6,364,856 B1 | 4/2002 | Ding et al. |
| 6,468,228 B1 | 10/2002 | Topel et al. |
| 6,685,718 B1 | 2/2004 | Wyzgala et al. |
| 6,800,083 B2 | 10/2004 | Hiblar et al. |
| 7,105,013 B2 * | 9/2006 | Durcan ...................... 623/1.11 |
| 7,252,674 B2 | 8/2007 | Wyzgala et al. |
| 7,641,620 B2 | 1/2010 | Wingler |
| 7,878,983 B2 | 2/2011 | Karpiel |
| 7,905,841 B2 * | 3/2011 | Richardson .................. 600/562 |
| 8,034,022 B2 | 10/2011 | Boatman |
| 8,057,496 B2 | 11/2011 | Fischer, Jr. |
| 8,070,691 B2 | 12/2011 | Desilets et al. |
| 8,100,881 B2 | 1/2012 | Hoffa |
| 8,123,769 B2 | 2/2012 | Osborne |
| 8,246,641 B2 | 8/2012 | Osborne et al. |
| 2012/0289982 A1 * | 11/2012 | Gunday et al. ............... 606/159 |

* cited by examiner

CYTOLOGY BALLOON

BACKGROUND

The present invention relates to cell collection devices. More particularly, the invention relates to a cell collection device having an inflatable balloon.

Cell collecting devices, or cytology devices, are well known in the art. A traditional cell collection device can be in the form of a cytology brush. A cytology brush can generally be used by being inserted into a body cavity of a patient, where the brush can contact the body cavity wall to collect cells. Cytology brushes are generally elongate, and include a distal end having a plurality of bristles extending radially outward. The brush can be in the form of a metallic coiled wire, and the bristles can be disposed between the coils. The coiled nature of the brush allows it to generally bend and navigate various tortuous body vessels. Additionally, the coils allow the brush to retain its pushability for delivering the brush through the anatomy.

However, the brushes can be ineffective in collecting a sufficient number of cells and can lead to irritation or bleeding during the cell collection process. The distal end of the brush is generally narrow and has a limited surface area for collecting cells. Moreover, the body vessels for which cell collection is desired can vary greatly from patient to patient. To collect the cells, the brush is inserted into the cavity and brushed against the cavity wall repeatedly, with pressure applied to the wall by the brush so that bristles contact the cavity. This brushing can often lead to bleeding, while collecting only a limited number of desired cells from a limited and inconsistent area of the cavity.

SUMMARY

A medical device for collecting cells is provided, the device comprising: an inflatable balloon being expandable from a compressed condition to an expanded condition, the balloon having proximal and distal portions and defining a longitudinal axis; a perforated sleeve surrounding the balloon, the perforated sleeve having proximal and distal portions, wherein the proximal portion of the sleeve is attached to the proximal portion of the balloon, the distal portion of the sleeve is attached to the distal portion of the balloon, and inflation of the balloon expands the sleeve radially outward; a plurality of openings disposed through sleeve, wherein the openings collect cells in response to engagement within a surface of a patient's body; and wherein the balloon and sleeve have a cell-collection configuration where the balloon is inflated to contact an inner surface of the sleeve and at least a portion of the plurality of openings.

In another form, the device further comprises an elongate catheter having proximal and distal portions, wherein the balloon is coupled to the distal portion of the catheter.

In another form, the sleeve is more rigid than the balloon.

In another form, the sleeve has a modulus of elasticity that is less than the modulus of elasticity of the balloon.

In another form, the sleeve is attached to the balloon using spot adhesion.

In another form, the sleeve is attached to the balloon along a longitudinal seam.

In another form, the sleeve and the balloon define an intermediate area therebetween when the balloon is deflated.

In another form, the sleeve includes an intermediate portion between the proximal and distal portion, and the intermediate portion is free from attachment to the balloon.

In another form, the sleeve comprises a generally rigid material.

In another form, the sleeve comprises a flexible material.

In another form, the sleeve is made from one of a silicone, HDPE, polyester, or Dacron material.

In another form, the sleeve has a compressed configuration and an expanded configuration, and the sleeve defines folds in the compressed configuration.

In another form, individual openings of the plurality of openings have a diameter in the range of 1 to 4 mm.

In another form, the device further comprises a protective sheath housing the balloon and sleeve therein, wherein the sheath is translatable relative to the balloon and the sleeve to expose the balloon and sleeve from the sheath.

In another form, a system for collecting cells from a body cavity is provided, the system comprising: an elongate catheter having proximal and distal portions and a defining a longitudinal axis therealong; a balloon coupled to the distal portion of the catheter, the balloon defining a cavity therein for being inflated to expand the balloon; a perforated sleeve surrounding the balloon and having a plurality of openings therethrough and proximal and distal ends, the proximal and distal ends being attached to the balloon; a first lumen defined by the catheter, the first lumen being in fluid communication with the balloon cavity; a second lumen defined by the catheter; a guidewire extending through the second lumen; and wherein the system includes a first radially compressed configuration and a second radially expanded condition, wherein the balloon contacts the sleeve in the expanded condition to force the sleeve radially outward.

In another form, individual openings of the plurality of openings have a diameter in the range of 1 to 4 mm for collecting cells therein.

In another form, the sleeve and the balloon define an intermediate space therebetween when the system is in the radially compressed configuration.

In another form, a method for collecting cells from a body cavity is provided, the method comprising: inserting, into a body cavity, an inflatable balloon having a sleeve attached thereto, the balloon being in a compressed condition and defining a longitudinal axis, and wherein the sleeve includes perforations therein and surrounds the balloon; delivering a fluid through a catheter into a cavity defined by the balloon; expanding the balloon in response to delivering the fluid into the cavity; contacting an inner surface of the sleeve with the balloon; in response to contacting the sleeve, expanding the sleeve radially outward; in response to expanding the sleeve radially outward, contacting a surface of the body cavity with the sleeve and the perforations thereof; reciprocating the sleeve against the surface of the body cavity to collect cells from the body cavity; and retracting the balloon and the sleeve from the body cavity.

In another form, expanding the sleeve includes stretching the sleeve.

In another form, expanding the sleeve comprises unfolding the sleeve.

In another form, the method further comprises deflating the balloon and creating an intermediate space between the balloon and the sleeve, wherein the cells are collected in the intermediate space.

In another form, the sleeve includes a proximal portion, a distal portion, and an intermediate portion therebetween, the proximal portion and distal portion are attached to the balloon, and the intermediate portion is free from attachment to the balloon.

In another form, the sleeve and the balloon define an intermediate space therebetween when the balloon is in the compressed configuration to trap cells.

DETAILED DESCRIPTION

Figure 1:
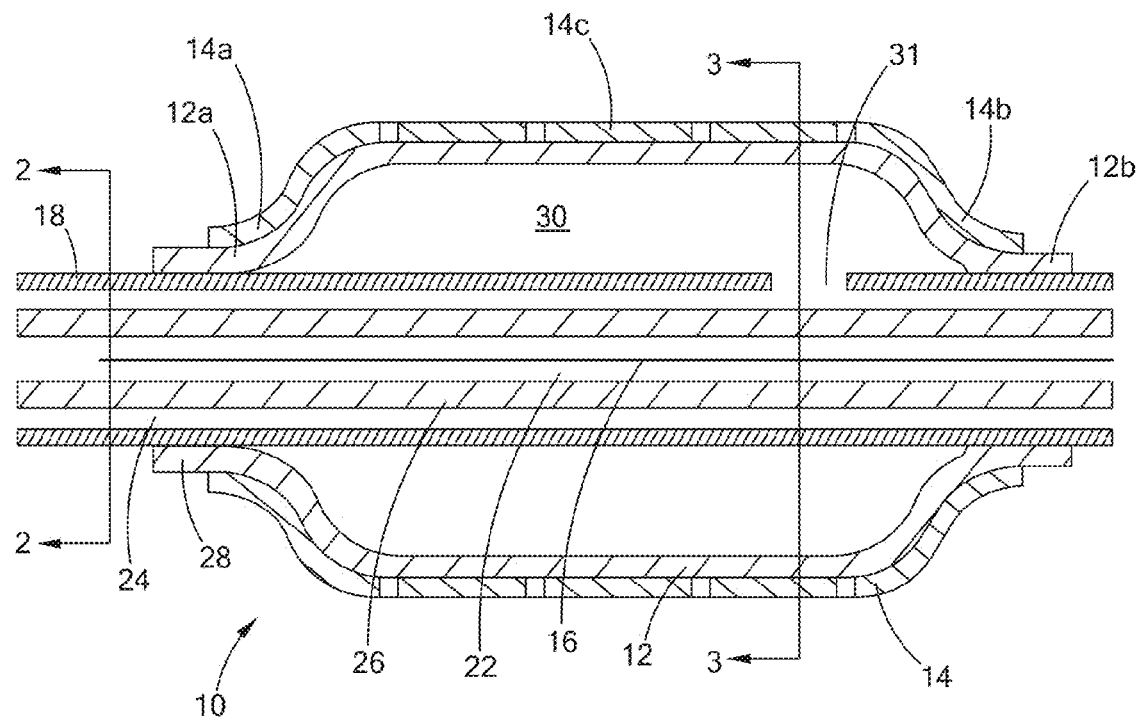
FIG. 1 is a schematic view of a medical device having a balloon, a sleeve surrounding the balloon, and a catheter attached to a proximal portion of the balloon.

The terms "proximal" and "distal" as used herein are intended to have a reference point relative to the user. Specifically, throughout the specification, the terms "distal" and "distally" shall denote a position, direction, or orientation that is generally away from the user and towards a target site, and the terms "proximal" and "proximally" shall denote a position, direction, or orientation that is generally towards the user and away from a target site. Thus, "proximal" and "distal" directions, portions of a device, or bodily regions, may depend on the point of entry for the procedure (e.g., percutaneously or laparoscopically or endoscopically).

Referring now to the drawings, FIGS. 1-7 illustrate a cell collection system 10 including an inflatable balloon 12 and a perforated sleeve 14 attached to the balloon 12. The system 10 can further include an elongate guidewire 16 over which the balloon 12 is delivered to a target site for cell collection.

The system 10 can further include an elongate catheter 18 having a proximal portion 18a and a distal portion 18b, with the balloon 12 attached to the distal portion. In one form, the balloon 12 can be in the form of a balloon catheter where the catheter 18 and balloon 12 are glued together as a general one piece structure; however, for the purposes of discussion, the catheter 18 and balloon 12 will be discussed as individual components.

Figure 2:
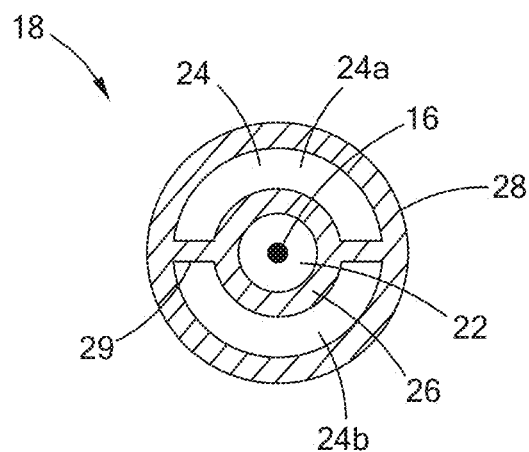
FIG. 2 is a cross-sectional view taken along the line 2-2.
Figure 3:
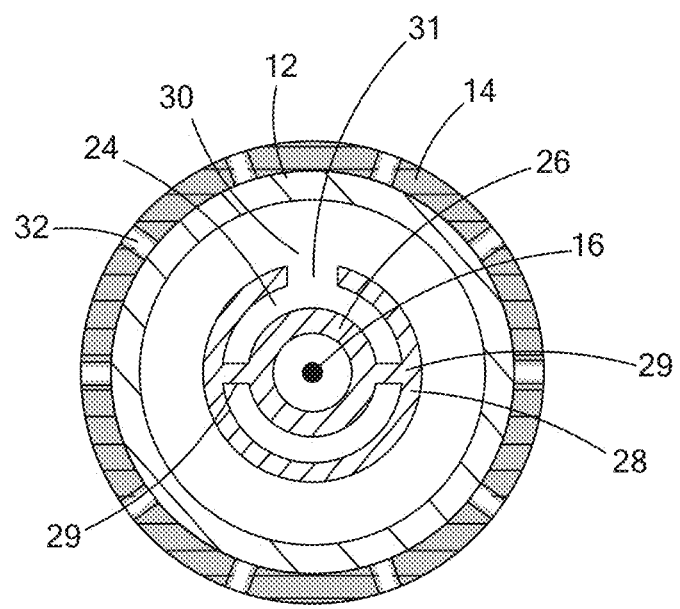
FIG. 3 is a cross-section view taken along the line 3-3.

With reference to FIGS. 1-3, the catheter 18, being mounted to the handle 20 can be in the form of a dual lumen catheter and include a first, inner lumen 22 and a second, outer lumen 24. The inner lumen 22 and outer lumen 24 can be generally coaxially aligned in a concentric pattern, such that the outer lumen 24 has a generally tubular cross-section, and the inner lumen 22 extends within the outer lumen 24. The inner lumen 22 and outer lumen 24 can be separated by an inner wall 26 that defines the inner lumen 22 within, and the outer lumen 24 can be surrounded by an outer wall 28 that, along with the inner wall 26, defines the outer lumen 24. The outer wall 28 can also serve as the outer wall of the catheter 18. The outer wall 28 and inner wall 26 can be joined via webbing 29 that extends at least partially along the outer lumen 24. In one form, the webbing can divide the outer lumen 24 into two distinct lumens 24a, 24b. The outer lumen 24 can be further divided by adding additional webbing. FIG. 2 illustrates this multiple lumen arrangement.

The outer lumen 24 can be coupled to a fluid source (not shown) for delivering an inflation fluid to the balloon 12 to inflate the balloon 12 (and allowing fluid to exit the balloon to deflate the balloon 12) in a manner known in the art.

In an alternative arrangement, the lumens 22 and 24 can be arranged in a side-by-side non-coaxial configuration. In this form, the lumens 22 and 24 would not have an inner/outer relationship but would operate similarly, with the lumen 22 receiving the guidewire 16 therethrough and the lumen 24 delivering fluid therealong. However, for the sake of discussion, the lumens 22 and 24 will be described as an inner lumen 22 and an outer lumen 24.

The inner lumen 24 can be used to receive the guidewire 16 therethrough to guide the catheter 18 and balloon 12 to the target site for collecting cells. The inner lumen 24 generally extends along the length of the catheter 18 and through the center of the balloon 12. Thus, the guidewire 16 can likewise extend along the length of the catheter 18 and through the balloon 12 toward the target site for cell collection. With the guidewire 16 extending through the balloon 12 and catheter 18, the balloon 12 and catheter 18 can be delivered along the guidewire 16 through the patient's anatomy toward the desired target site.

As known in the art, the balloon 12 can be inflated and deflated by delivering fluid through the outer lumen 24. The balloon 12 defines a cavity 30 that increases in volume and diameter as it inflated thereby increasing the outer diameter of the balloon 12. The outer wall 28 can include a port 31 that provides fluid communication between the outer lumen 24 and the balloon cavity 30 (see FIGS. 1 and 3). The balloon 12 can also be deflated to decrease the size of the balloon 12.

In one form, the balloon 12 can be made from a generally soft material including, but not limited to, nylon, PEBAX, polyamide, polyethylene, terephthalate, silicone, or the like. In another form, the balloon 12 can be made from a more rigid material including, but not limited to, nylon, PEBAX, polyamide, polyethylene, terephthalate, or the like. Other possible materials for the balloon 12 can include polyurethane, PVE, other poly-olefins, and PTFE. It will be appreciated that other suitable materials for balloons or balloon catheters known in the art can also be used.

The length and diameter of the balloon 12 can be tailored to correspond to the body vessel or cavity where cell collection is desired. The diameter of the balloon 12 refers to the diameter in the generally inflated condition. For the esophagus, the length of the balloon 12 can be in the range of 15-30 mm and the diameter can be about 20-25 mm. For the biliary system, the length of the balloon 12 can be in the range of 5-20 mm and the diameter can be about 5-15 mm. For the colon, the length of the balloon 12 can be about 20-50 mm and the diameter can be about 25-80 mm; however, in clinical use at the colon, the diameter of the balloon 12 may not need to be any more than 50 mm. In pulmonary or other areas, the length of the balloon 12 can be about 5-10 mm and the diameter can be about 3-10 mm. Of course, these ranges and uses are merely exemplary, and other sizes for the balloon 12 can also be used to fit the needs of the user and the desired target area for collecting cells. The ranges listed are intended to correspond to the various body lumens in which the balloon 12 can be inserted, and it will be appreciated that atypical sizing or disease such that the balloon 12 can be sized to correspond to the atypical sizing outside the above listed range. Additionally, the balloon 12 can be sized to correspond to different anatomy shapes. For example, while the balloon 12 has been described as having a diameter, it will be appreciated that the balloon 12 is not exactly tubular, and the shape of the balloon 12 can be adjusted to various tapering, oblong, or non-tubular anatomy shapes.

Figure 1A:
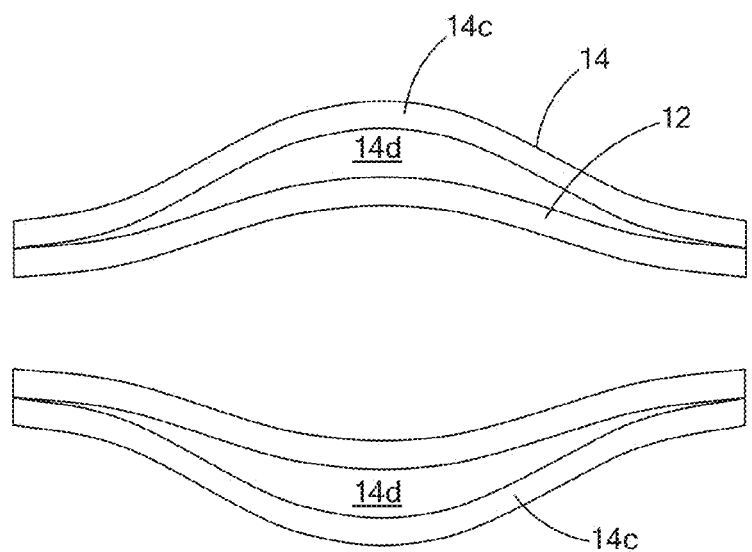
FIG. 1A is a schematic view showing an intermediate space between the sleeve and the balloon.

With reference to FIG. 1, the perforated sleeve 14 can be attached to the balloon 12 for being expanded along with the balloon 12. The perforated sleeve includes a proximal end 14a and a distal end 14b. The proximal end 14a can be attached to a proximal portion 12a of the balloon 12, and the distal end 14b can be attached to the distal end 12b of the balloon 12. The sleeve 14 can be attached using an adhesive, ultrasonic welding, or another attachment type known in the art. In another form, the sleeve 14 can be attached to the balloon 12 via point adhesion at points extending longitudinally along the balloon 12 and the sleeve 14. In another form, the sleeve 14 can be attached to the balloon 12 along a longitudinal seam therebetween. In another form, an intermediate portion 14c of the sleeve 14 can remain generally free from attachment with the balloon 12. Thus, the sleeve 14 can be generally loose relative to the balloon 12 at various locations, thereby defining an intermediate space 14d between the balloon 12 and sleeve 14 when the balloon 12 is deflated (see FIG. 1A).

The sleeve 14 can be made from a generally rigid material such as nylon, PEBAX, polyamide, polyethylene, or terephthalate. The sleeve 14 can alternatively be made from a generally flexible material such as silicone, HDPE, polyester, or Dacron. Other materials for the sleeve 14 can include eptfe, PTFE, Nylon, Nitinol, Stainless Steel, and Hydrogel (such as cross-linked polymer structure). Of course, other materials not listed here could also be used. The sleeve 14 can be produced by a variety of methods including, but not limited to, braiding, weaving, laser cutting, heat imprinting, meshing, molding, or extruding.

The perforated sleeve 14 can be sized to correspond generally to the size of the balloon 12. For example, if the balloon 12 is 10 mm long and 5 mm in diameter, the sleeve 14 can be sized slightly larger depending on the thickness of the balloon 12. For example, if the thickness of the sleeve material is approximately 1 mm, the diameter of the sleeve 14 can be approximately the diameter of the balloon 12 plus 2 mm. The inner diameter of the sleeve 14 is preferably less than or equal to the maximum outer diameter of the balloon 12 when inflated. In the event the sleeve 14 has an inner diameter that is less than the outer diameter of the balloon 12 when inflated, then the sleeve 14 can either stretch (if the sleeve 14 is made from a flexible material) or prevent the balloon 12 from being inflated to its maximum diameter (if the sleeve 14 is made from a rigid material). FIG. 3 illustrates an arrangement of the balloon 12 being inflated to expand the sleeve 14.

Figure 4:
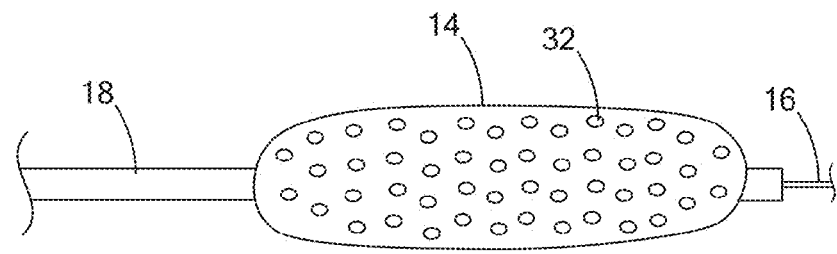
FIG. 4 is a front view of the medical device of claim 1 showing perforations of the sleeve.

With reference to FIGS. 3 and 4, the perforated sleeve 14 can include a plurality of perforations or openings 32 disposed about the outer surface of the sleeve 14. Generally speaking, the openings 32 can be disposed around the majority of the sleeve 14 to create a rough surface relative to a sleeve without perforations or openings. The openings 32 can be used to collect the cells from the target site within the patient, as further described below. The diameter of the openings 32 can vary depending on the overall size of the balloon 12 and sleeve 14. In one form, the diameter of the openings 32 can be in the range of 1-4 mm. It will be appreciated that other ranges can be used. Moreover, the total number of openings 32 and spacing between the openings 32 can vary as well. For example, the spacing between openings could be between 2 and 5 mm, but could also be greater if desired. The openings 32 have been described as being generally circular and having a diameter; however, other shapes of the openings could also be used, such as a square, a star, an oval, another polygonal shape, or the like. If these non-circular shapes are used, the above sizes can generally correspond to the width of the opening 32. Of course, it will be appreciated that various other sizes could also be used.

Of course, the strength of the sleeve 14 can decrease as the number of openings 32 increases, the size increase, or the space between them decreases. Thus the overall size of the sleeve 14 can determine the appropriate size and number of openings 32 to maximize cell collection while maintaining the strength of the sleeve 14. In the case when the sleeve 14 is made from a flexible material that is stretched in response to inflation of the balloon 12, the openings 32 can become more rigid due to the stretching, thereby enabling improved scraping and cell collection by the sleeve 14.

Figures 5, 6:
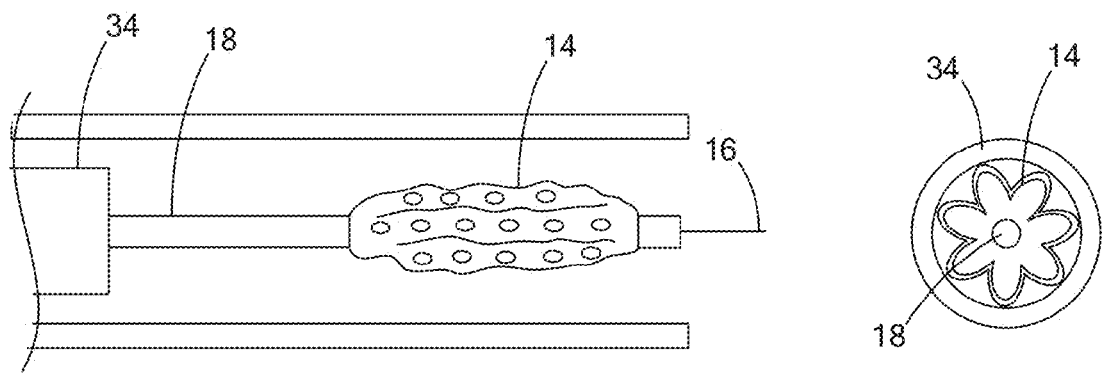
FIG. 5 is side view of a sleeve in a compressed condition within a sheath.
FIG. 6 is a front view of the sleeve exposed from the sheath within a body cavity.
Figure 7:
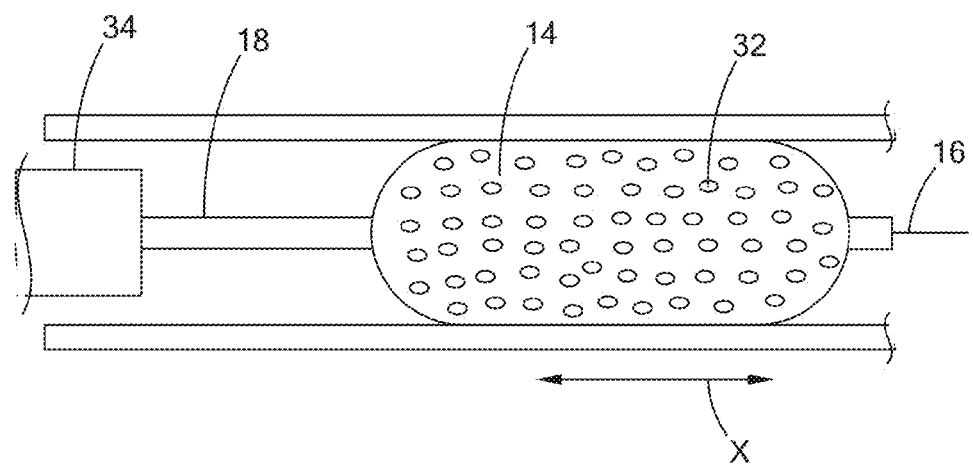
FIG. 7 is a side view of the sleeve in an expanded condition in contact with a surface of the body cavity.

With reference to FIGS. 5 and 6, the balloon 12, catheter 18, and sleeve 14 can each be housed within a delivery sheath 34 for delivery to the target site along the guidewire 16. When housed in the delivery sheath 34, the balloon 12 and sleeve 14 can be in a compressed delivery configuration. In this form, the balloon 12 and sleeve 14 can be folded onto themselves to reduce their outer profile and fit within the sheath 34. When delivered to the target site, the sheath 34 can be retracted to expose to the balloon 12 and the sleeve 14 (or the balloon 12 and sleeve 14 can be advanced out of the sheath 34). With the balloon 12 and sheath 14 exposed to the target site outside of the sheath 34, the balloon 12 can be inflated, expanding the balloon 12 and sleeve 14 to an expanded cell collecting condition. FIG. 6 illustrates the sleeve 14 being exposed from the sheath 34 and in the compressed condition. FIG. 7 illustrates the sleeve 14 in the expanded condition in response to inflation of the balloon 12.

Alternatively, the sleeve 14 can be made from a generally flexible and expandable material, so that the sleeve 14 is generally not folded in the compressed condition. When the balloon 12 is inflated, the sleeve 14 can stretch and expand along with the balloon 12 expansion to increase the size of the sleeve 14 to meet the size of the target site.

It should be noted that the balloon 12 and sleeve 14 can be used without a guidewire 16 and the optional protective sheath 34. For example, in instances where direct visualization of the balloon 12 and sleeve 14 at the target site is possible, the guide wire 16 may not be helpful in locating the balloon 12 and sleeve 14. Similarly, while the protective sleeve 34 helps deliver the balloon 12 and sleeve 14 to the target site while shielding them from the patient's anatomy, this may not be desirable or necessary. The catheter 18 could also be in the form of a single lumen catheter if a guidewire is not used, or if the guidewire 16 does not need to travel along the length of the catheter 18. In such a case, a single lumen can be used for inflating the balloon 12.

Having described the general structure of the device 10, the use of the device 10 will now be described.

The device 10 can be introduced into the body either directly into an orifice or percutaneously in a manner known in the art. The device 10 could be delivered using a scope or other suitable delivery tool.

The balloon 12 and sleeve 14 can be in the compressed delivery condition, as shown in FIG. 5, with the balloon 12 deflated and the overall profile of the balloon 12 and sleeve 14 reduced. The balloon 12 and 14 can be housed within the sheath 34 in the event the sheath 34 is used.

The balloon and sleeve 14 can be routed through the patient's anatomy toward the desired target area. The location of the balloon 12 and sleeve 14 can be monitored using known monitoring methods. In one form, they can be monitored by direct visualization. In another form, they can be monitored using endoscopic guidance. In another form, they can be monitored using fluoroscopic guidance.

Once the balloon 12 and sleeve 14 are located at the desired area, the balloon 12 and sleeve 14 can be exposed from within the sheath 34, if used. The sheath 34 can be retracted, the balloon and sleeve 14 pushed outwardly from the sheath 34, or a combination of both to expose the balloon 12 and sleeve 14, as shown in FIG. 6.

With reference to FIG. 7, the balloon 12 can then be inflated by delivering an inflation fluid to the cavity 30 of the balloon 12 in a manner known in the art. The diameter of the balloon 12 will increase in response to filling the cavity 30. The sleeve 14, being attached to and surrounding the balloon 12, will likewise increase in diameter toward the body vessel wall. The sleeve 14 will preferably make contact with the wall around its circumference to increase the area of cell collection and total number of cells collected relative to a traditional cytology brush.

With the balloon 12 and sleeve 14 expanded, the catheter 18 can be reciprocated slightly (illustrated by arrow X in FIG. 7) to cause the balloon 12 and sleeve 14 to move fore and aft, thereby making contact with the body vessel to collect cells therefrom. The perforations or openings 32 in the sleeve 14 will collect the cells therein, and the fore and aft reciprocation will cause the openings to contact a greater surface area. The openings 32 in the sleeve 14 can create a relatively rough surface for collecting the cells relative to a smooth balloon or sleeve, but the roughness remains less than that of a traditional cytology brush. Thus, patient trauma can be limited and the collection can be generally limited to cells without causing blood to be collected, as well.

Once the reciprocation of the device is completed, the balloon 12 can be deflated to reduce its diameter, thereby allowing the diameter of the sleeve 14 to be reduced as well. FIG. 6 illustrates this compressed condition. When the balloon 12 deflates, the intermediate space 14d between the balloon 12 and sleeve 14 can "catch" and retain the cells that were collected by the openings 32. The balloon 12 and sleeve 14 can be drawn back into the sheath 34, if used, in a manner known in the art. The balloon 12 and sleeve 14 can be retracted from the patient's body, where the collected cells can be processed and investigated.

As a person skilled in the art will readily appreciate, the above description is meant as an illustration of implementation of the principles this invention. This description is not intended to limit the scope or application of this invention in that the invention is susceptible to modification, variation, and change, without departing from the spirit of this invention, as defined in the following claims.

What is claimed is:

1. A medical device for collecting cells, the device comprising:
    an inflatable balloon being expandable from a compressed condition to an expanded condition, the balloon having proximal and distal portions and defining a longitudinal axis;
    a perforated sleeve surrounding the balloon, the perforated sleeve having proximal and distal portions, wherein the proximal portion of the sleeve is attached to the proximal portion of the balloon, the distal portion of the sleeve is attached to the distal portion of the balloon, and inflation of the balloon expands the sleeve radially outward, wherein the inner diameter of the sleeve is less than or equal to the maximum outer diameter of the balloon;
    a plurality of openings disposed through sleeve, wherein the openings collect cells in response to engagement within a surface of a patient's body; and
    wherein the balloon and sleeve have a cell-collection configuration where the balloon is inflated to contact an inner surface of the sleeve and at least a portion of the plurality of openings, wherein, when inflated, the balloon blocks openings of the plurality of openings to trap and collect cells with the blocked openings; and
    wherein there is no intermediate structure radially between the balloon and the perforated sleeve, wherein the balloon will not be limited from contacting the inner surface of the sleeve by intermediate structure and will not be limited from blocking the openings by intermediate structure.

2. The device of claim 1 further comprising an elongate catheter having proximal and distal portions, wherein the balloon is coupled to the distal portion of the catheter.

3. The device of claim 1, wherein the sleeve is more rigid than the balloon.

4. The device of claim 1, wherein the sleeve has a modulus of elasticity that is less than the modulus of elasticity of the balloon.

5. The device of claim 1, wherein the sleeve is attached to the balloon along a longitudinal seam.

6. The device of claim 1, wherein the sleeve and the balloon define an intermediate area therebetween when the balloon is deflated.

7. The device of claim 1, wherein the sleeve includes an intermediate portion between the proximal and distal portion, and the intermediate portion is free from attachment to the balloon.

8. The device of claim 1, wherein the sleeve comprises a generally rigid material.

9. The device of claim 1, wherein the sleeve comprises a flexible material.

10. The device of claim 1, wherein the sleeve has a compressed configuration and an expanded configuration, and the sleeve defines folds in the compressed configuration.

11. The device of claim 1, wherein individual openings of the plurality of openings have a diameter in the range of 1 to 4 mm.

12. The device of claim 1 further comprising a protective sheath housing the balloon and sleeve therein, wherein the sheath is translatable relative to the balloon and the sleeve to expose the balloon and sleeve from the sheath.

13. A system for collecting cells from a body cavity, the system comprising:
    an elongate catheter having proximal and distal portions and a defining a longitudinal axis therealong;
    a balloon coupled to the distal portion of the catheter, the balloon defining a cavity therein for being inflated to expand the balloon;
    a perforated sleeve surrounding the balloon and having a plurality of openings therethrough and proximal and distal ends, the proximal and distal ends being attached to the balloon, wherein the inner diameter of the sleeve is less than or equal to the maximum outer diameter of the balloon;
    a first lumen defined by the catheter, the first lumen being in fluid communication with the balloon cavity;
    a second lumen defined by the catheter;
    a guidewire extending through the second lumen; and
    wherein the system includes a first radially compressed configuration and a second radially expanded condition, wherein the balloon contacts the sleeve in the expanded condition to force the sleeve radially outward, wherein, when inflated, the balloon blocks openings of the plurality of openings to trap and collect cells with the blocked openings; and wherein there is no intermediate structure radially between the balloon and the perforated sleeve, wherein the balloon will not be limited from contacting the inner surface of the sleeve by intermediate structure and will not be limited from blocking the openings by intermediate structure.

14. The system of claim 13, wherein individual openings of the plurality of openings have a diameter in the range of 1 to 4 mm for collecting cells therein.

15. The system of claim 13, wherein the sleeve and the balloon define an intermediate space therebetween when the system is in the radially compressed configuration.

16. A method for collecting cells from a body cavity, the method comprising:
- inserting, into a body cavity, an inflatable balloon having a sleeve attached thereto, the balloon being in a compressed condition and defining a longitudinal axis, and wherein the sleeve includes perforations therein and surrounds the balloon, wherein the inner diameter of the sleeve is less than or equal to the maximum outer diameter of the balloon, and wherein there is no intermediate structure radially between the balloon and the perforated sleeve, wherein the balloon will not be limited from contacting the inner surface of the sleeve by intermediate structure and will not be limited from blocking the openings by intermediate structure;
- delivering a fluid through a catheter into a cavity defined by the balloon; expanding the balloon in response to delivering the fluid into the cavity; contacting an inner surface of the sleeve with the balloon;
- in response to contacting the sleeve, expanding the sleeve radially outward, and blocking perforations of the plurality of perforations of the sleeve;
- in response to expanding the sleeve radially outward, contacting a surface of the body cavity with the sleeve and the perforations thereof;
- reciprocating the sleeve against the surface of the body cavity and contacting the surface of the body cavity with the perforations of the sleeve to collect cells from the body cavity and trap the cells within the blocked perforations; and
- retracting the balloon and the sleeve from the body cavity.

17. The method of claim 16, wherein expanding the sleeve includes stretching the sleeve.

18. The method of claim 16, wherein expanding the sleeve comprises unfolding the sleeve.

19. The method of claim 16 further comprising deflating the balloon and creating an intermediate space between the balloon and the sleeve, wherein the cells are collected in the intermediate space.

20. The method of claim 16, wherein the sleeve includes a proximal portion, a distal portion, and an intermediate portion therebetween, the proximal portion and distal portion are attached to the balloon, and the intermediate portion is free from attachment to the balloon.

21. The method of claim 20, wherein the sleeve and the balloon define an intermediate space therebetween when the balloon is in the compressed configuration to trap cells.

22. The device of claim 1, wherein the balloon seals against the inner surface of the sleeve around the blocked openings.

23. The device of claim 1, wherein, when the balloon is inflated, the sleeve has a uniform outer diameter.

24. The device of claim 1, wherein, when the balloon is inflated, the sleeve has a smooth outer surface between the openings.

25. The device of claim 1, wherein cells collected within the blocked openings fall into an intermediate space between the sleeve and the balloon only when the balloon is deflated.

26. The method of claim 16, wherein the sleeve is configured such that cells collected by the blocked perforations will fall into an intermediate space between the sleeve and the balloon only when the balloon is deflated.

27. The device of claim 1, wherein, when the balloon is inflated to block the openings of the plurality of openings, an outer surface of the perforated sleeve defines an outermost surface of the device.

\* \* \* \* \*